(12) United States Patent
Partington et al.

(10) Patent No.: US 9,950,968 B2
(45) Date of Patent: Apr. 24, 2018

(54) PROCESS FOR PREPARING ETHENE

(71) Applicant: Technip E&C Limited, Milton Keynes (GB)

(72) Inventors: Stephen Roy Partington, East Yorkshire (GB); Nigel Stewart Brown, East Yorkshire (GB); Michael Keith Lee, East Yorkshire (GB); Mark Julian Howard, East Yorkshire (GB)

(73) Assignee: Technip E&C Limited, Milton Keynes (GB)

( * ) Notice: Subject to any disclaimer, the term of this patent is extended or adjusted under 35 U.S.C. 154(b) by 0 days.

(21) Appl. No.: 15/128,243

(22) PCT Filed: Apr. 1, 2015

(86) PCT No.: PCT/EP2015/057263
§ 371 (c)(1),
(2) Date: Sep. 22, 2016

(87) PCT Pub. No.: WO2015/150497
PCT Pub. Date: Oct. 8, 2015

(65) Prior Publication Data
US 2017/0121238 A1    May 4, 2017

(30) Foreign Application Priority Data
Apr. 2, 2014 (EP) .................................. 14163224

(51) Int. Cl.
| C07C 1/24 | (2006.01) |
| B01J 23/30 | (2006.01) |
| B01J 35/10 | (2006.01) |
| B01J 37/02 | (2006.01) |
| B01J 27/188 | (2006.01) |

(52) U.S. Cl.
CPC .................. *C07C 1/24* (2013.01); *B01J 23/30* (2013.01); *B01J 35/1019* (2013.01); *B01J 35/1042* (2013.01); *B01J 35/1061* (2013.01); *B01J 37/0201* (2013.01); *B01J 27/188* (2013.01); *B01J 2523/00* (2013.01); *C07C 2523/30* (2013.01); *Y02P 20/52* (2015.11)

(58) Field of Classification Search
CPC ................ B01J 2523/00; B01J 2523/41; B01J 2523/69; B01J 23/30; B01J 27/188; B01J 35/1019; B01J 35/1042; B01J 35/1061; B01J 37/0201; C07C 1/24; C07C 11/04; C07C 2523/30
See application file for complete search history.

(56) References Cited

FOREIGN PATENT DOCUMENTS

| EP | 1925363 | 5/2008 | |
| WO | WO-2007/003899 | 1/2007 | |
| WO | WO-2007/063281 | 6/2007 | |
| WO | WO 2007063279 A1 * | 6/2007 | ............... C07C 1/24 |
| WO | WO-2008/138775 A1 | 11/2008 | |

OTHER PUBLICATIONS

European Search Report for related application No. EP 14163224.0, dated Sep. 16, 2014.
International Search Report for related International application No. PCT/EP2015/057263, dated Jun. 12, 2015.
Barrett et al., "The Determination of Pore Volume and Area Distributions in Porous Substances. I. Computations from Nitrogen Isotherms," J Amer. Chem Soc. 73, pp. 373-380 (1951).
Brunauer et al., "Adsorption of Gases in Multimolecular Layers," J Amer. Chem Soc. 60, pp. 309-319 (1938).

* cited by examiner

*Primary Examiner* — Sharon Pregler
(74) *Attorney, Agent, or Firm* — Porzio, Bromberg & Newman P.C.

(57) ABSTRACT

The present invention provides a process for the preparation of ethene by vapor phase chemical dehydration of a feed comprising ethanol, said process comprising contacting the feed with a supported heteropolyacid catalyst in a reactor, wherein the feed temperature is at least 250° C. and the pressure inside the reactor is at least 0.80 MPa but less than 1.80 MPa.

20 Claims, 2 Drawing Sheets

PROCESS FOR PREPARING ETHENE

Figure 1:
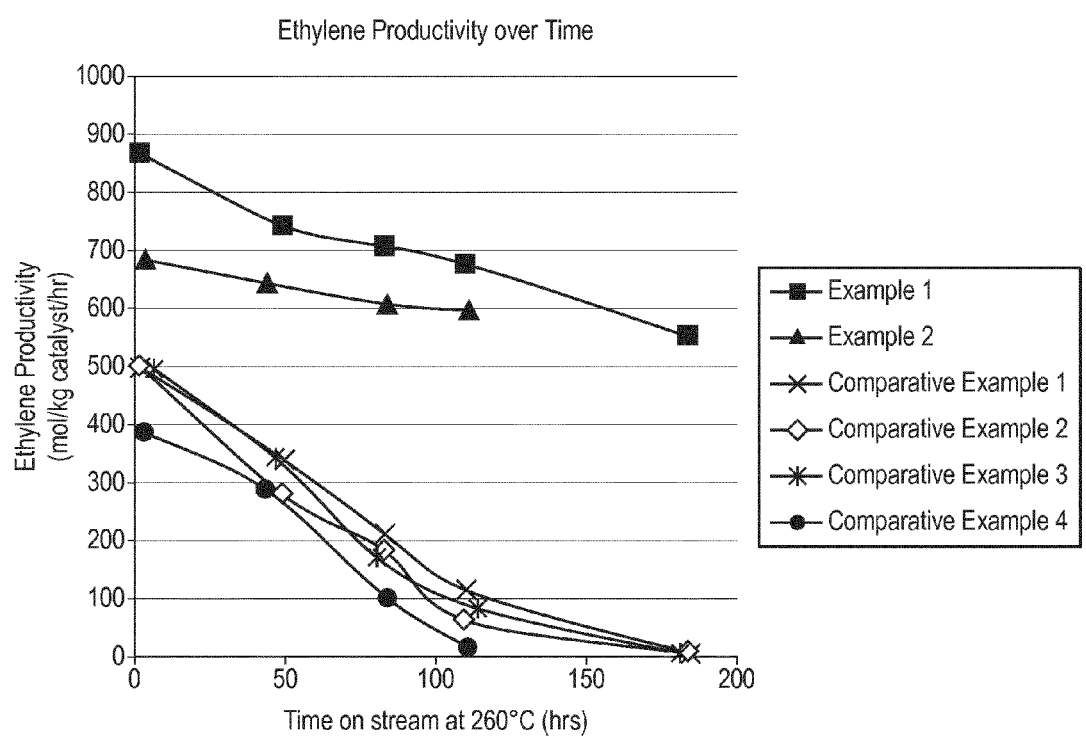

The present invention relates to a process for producing ethene by the vapour phase dehydration of ethanol using a heteropolyacid catalyst.

Ethene is an important commodity chemical and monomer which has traditionally been produced industrially by the steam or catalytic cracking of hydrocarbons derived from crude oil. However there remains an increasing need to find alternative economically viable methods of making this product. By virtue of its ready availability from the fermentation of biomass and synthesis gas based technologies, ethanol is emerging as an important potential feedstock from which ethene can be made in the future.

The production of ethene by the vapour phase chemical dehydration of ethanol is a well-known chemical reaction which has been operated industrially for many years (see for example Kirk Othmer Encyclopaedia of Chemical Technology (third edition), Volume 9, pages 411 to 413). Traditionally this reaction has been carried out in the presence of an acid catalyst such as activated alumina or supported phosphoric acid.

In recent years attention has turned to finding alternative catalysts having improved performance. This has led to the use of supported heteropolyacid catalysts, such as those disclosed in EP1925363, which have the benefit of improved selectivity, productivity and reduced ethane formation following the dehydration of a feedstock comprising ethanol and ethoxyethane for the production of ethene. This is desirable because firstly ethane is an undesirable by-product and secondly its separation from ethene on a large scale is both difficult and energy intensive. Related documents WO 2007/063281 and WO 2007/003899 also disclose modes of carrying out dehydration of oxygenate feedstocks with supported heteropolyacid catalysts.

In the dehydration process, a feed typically comprising ethanol, optionally water and other components (e.g. ethoxyethane) is continuously fed to a reactor containing a bed of heteropolyacid catalyst and the products continuously removed. Under steady state conditions, the feed entering the reactor is rapidly converted near the inlet into an equilibrium mixture of water, ethanol and ethoxyethane (the product of a rapid first stage dehydration of the ethanol). Such processes are typically conducted at elevated temperature and pressure. In exemplified dehydration processes employing heteropolyacid catalysts disclosed in the prior art, the temperature of the reaction does not exceed 240° C., whilst the sum of the partial pressures of the reactants is typically 2 MPa (i.e. excluding partial pressures of inert diluents, such as nitrogen).

It has been found that productivity in a process for producing ethene by the vapour phase dehydration of ethanol using a heteropolyacid catalyst is improved by operating at high temperature; in particular at temperatures higher than those exemplified in the prior art. Although it has now become desirable to operate at the highest possible temperatures to increase ethene productivity, whilst maintaining appropriate selectivity, one problem that has hitherto not been acknowledged relates to catalyst deactivation. It has been found that when operating the dehydration process at high temperature, deactivation of the heteropolyacid catalyst is exacerbated. Without being bound by any particular theory, this is believed to occur as a result of undesirable side reactions with high activation energies, which contribute to deactivation, becoming more prevalent as a result of the higher temperatures being used.

It is known that oxygenate dehydration can lead to carbon build-up on acidic catalysts, such as silicotungstic-$SiO_2$, which leads to catalyst deactivation. Carbon lay-down leading to catalyst deactivation is, for instance, mentioned in WO 2008/138775. That document reports such deactivation in a heteropolyacid catalysed oxygenate dehydration conducted at atmospheric pressure and comprising use of a sequence of vapour phase feeds, including ethanol in helium and diethyl ether in helium. Deactivation results obtained in respect of an equivalent operation conducted at an elevated pressure of 2.1 MPa (21 bara), that is, the sum of the partial pressures of the reactants excluding inert diluents/components, were reported as being consistent with those observed at atmospheric pressure. This suggests that carbon lay-down is unaffected by the pressure of the operation.

Replacement of the catalyst in a dehydration system is labour intensive, has significant materials costs and involves temporarily shutting down what is likely to be a continuous process, which has detrimental impact on product output. Consequently, there is likely to be a greater motivation to accept more moderate productivity by operating at lower temperature in order to benefit from longer catalyst lifetime.

It has now surprisingly been found that catalyst lifetime during operation at high temperatures can be extended by performing the dehydration process at lower pressures than exemplified in the prior art. Contrary to what is suggested in the prior art, by performing the dehydration reaction at certain intermediate pressures, the temperature of the reaction may be increased to enhance ethene productivity, without exacerbating catalyst deactivation. Consequently, the particular combination of process features according to the present invention has the benefit of maximising productivity in a dehydration process over an extended catalyst lifetime.

According to the present invention, there is provided a process for the preparation of ethene by vapour phase chemical dehydration of a feed comprising ethanol (and preferably water and/or ethoxyethane), said process comprising contacting the feed with a supported heteropolyacid catalyst in a reactor, wherein the feed temperature is at least about 250° C. and the pressure inside the reactor is at least about 0.80 MPa but less than about 1.80 MPa.

Reference herein to the pressure inside the reactor corresponds to the sum of the partial pressures of the reactants, namely those of ethanol and (if present) water and ethoxyethane, as well as the partial pressure of the ethylene product. Unless otherwise indicated herein, partial pressures of inert diluents, such as helium and nitrogen, or other inert components are excluded from the total stated pressure. Thus, reference to reactor pressure herein is in accordance with the formula: $P_{reactor} = P_{water} + P_{ethanol} + P_{ethoxyethane} + P_{ethylene}$.

As will be appreciated by the skilled person, there is often a pressure drop that occurs in a dehydration reactor between the point where the feed stream enters the reactor and that where the effluent stream emerges from the reactor. For example, the feed stream pressure may be at about 1.4 MPa whilst the effluent stream may be at a pressure of about 1.0 MPa; corresponding to a pressure drop of about 0.4 MPa. As a consequence, there is, to a varying extent, an internal pressure gradient which exists inside the reactor itself. It is therefore to be understood that reference herein to the "pressure inside the reactor", or the "internal pressure of the reactor", means any pressure falling within the pressure range defined by the above-mentioned internal pressure gradient. The pressure inside the reactor itself therefore lies between the feed stream pressure and the effluent stream pressure.

It has been surprisingly found that the combination of operating conditions according to the present invention maximises ethene productivity whilst significantly reducing the level of heteropolyacid catalyst deactivation which would otherwise result from conducting the reaction at higher temperature than is conventional for this type of reaction. Mechanisms by which the supported heteropolyacids are believed to undergo deactivation include: i) neutralisation by inorganic cations, such as ammonia/ammonium cations, and organic nitrogen-containing compounds; ii) carbon deposition; and iii) decomposition of the heteropolyacid to its constituent oxides.

Deactivation as a result of neutralisation by inorganic cations and organic nitrogen-containing compounds may be mitigated by committing the ethanol based raw materials to a clean-up procedure to remove the neutralising species. Without wishing to be bound by any particular theory, it is believed that the operating conditions according to the process of the present invention largely eliminate any deactivation of the heteropolyacid catalyst as a result of carbon deposition and decomposition. A lower pressure of operation is believed to reduce the amount of adsorbed species on the surface of the catalyst, which may lead to deactivation. Meanwhile, operating at pressures above atmospheric, for instance at pressures of at least about 0.80 MPa inside the reactor, is believed to help reduce carbon deposition. As a consequence, the catalyst lifetime is significantly extended, which has clear economic benefits relating to re-use and replacement of the catalyst, as well as the reduction of waste. The operating conditions of the present invention thus correspond to a narrow window within which significant catalyst deactivation is avoided, whilst ethylene productivity is promoted.

The dehydration of the feedstock according to the present invention is believed (Chem. Eng Comm. 1990, 95, 27 to 39) to proceed by either the direct dehydration to olefin(s) and water (Equation 1); or via an ether intermediate (Equations 2 and 3).

$$\text{EtOH} \rightleftharpoons = + H_2O \quad (1)$$

$$\text{EtOH} \rightleftharpoons Et_2O + H_2O \quad (2)$$

$$Et_2O \rightleftharpoons = + EtOH \quad (3)$$

The direct conversion of the ether to two moles of olefin and water has also been reported (Chem. Eng. Res. and Design 1984, 62, 81 to 91). All of the reactions shown above are typically catalysed by Lewis and/or Bronsted acids. Equation 1 shows the endothermic direct elimination of ethanol to ethene and water; competing with Equation 1 are Equations 2 and 3 i.e. the exothermic etherification reaction (Equation 2), and the endothermic elimination of ethoxyethane to produce ethene and ethanol (Equation 3). However, the dehydration reaction of ethanol to ethene is overall said to be endothermic.

The present invention provides a process for the preparation of ethene by vapour phase chemical dehydration of a feed comprising ethanol, (and preferably further comprising water and/or ethoxyethane), said process comprising contacting the feed with a supported heteropolyacid catalyst in a reactor, wherein the feed temperature is at least about 250° C. and the pressure inside the reactor is at least about 0.80 MPa but less than about 1.80 MPa.

Preferably, the amount of water in the feed of the process of the present invention is at most about 50 wt. %, more preferably at most about 20 wt. %, most preferably at most about 10 wt. %, or even at most about 7 wt. %, based on the total weight of water, ethanol and ethoxyethane in the reactant feed stream. Preferably, the amount of water in the reactant feed stream is at least about 0.1 wt. %, more preferably at least about 0.5 wt. % and most preferably at least about 1 wt. %, based on the total weight of water, ethanol and ethoxyethane in the reactant feed stream.

The liquid product stream following olefin removal comprises mostly unreacted ethanol, diethyl ether and water. The applicants have found that it is particularly preferable to recycle the major portion of the alcohols and ethers back to the vapour phase dehydration reactor after water by-product removal.

In some embodiments of the invention, the feed comprises an inert, non-condensable diluent. In other embodiments, an inert, non-condensable diluent is added down the catalyst bed, or between multiple catalyst beds arranged in series or in parallel, if used. Preferred diluents comprise nitrogen, helium, ethene and/or saturated hydrocarbons, for example hexanes, 2-methylpropane or n-butane. More preferably, the feed diluent is selected from nitrogen and/or helium.

As regards further preferred operating conditions of the process of the present invention, the feed temperature for the dehydration reaction is preferably at least about 252° C., more preferably the feed temperature for the reaction is at least about 255° C., even more preferably the feed temperature for the reaction is at least about 260° C., even more preferably still the feed temperature for the reaction is at least about 280° C. Most preferably, the feed temperature for the reaction is at least about 300° C. The upper limit of the feed temperature is below the temperature at which selectivity for ethene is negatively impacted and/or one which is overly energy intensive. Preferably, the upper limit of the feed temperature is about 350° C., more preferably about 325° C. Thus, preferred feed temperature ranges for the dehydration reaction include: a) at least about 252° C. to about 350° C.; b) at least about 252° C. to about 325° C.; c) at least about 255° C. to about 350° C.; d) at least about 255° C. to about 325° C.; e) at least about 260° C. to about 350° C.; f) at least about 260° C. to about 325° C.; g) at least about 280° C. to about 350° C.; h) at least about 280° C. to about 325° C.; i) at least about 300° C. to about 350° C.; and j) at least about 300° C. to about 325° C.

In a preferred embodiment, the reactor has an internal pressure of from about 0.90 MPa to about 1.60 MPa. More preferably, the reactor has an internal pressure of from about 0.95 MPa to about 1.30 MPa. Most preferably, the reactor has an internal pressure of from about 1.00 MPa to about 1.20 MPa.

Preferably, the feed stream pressure is from about 1.00 MPa to about 1.80 MPa, more preferably the feed stream pressure is from about 1.20 MPa to about 1.60 MPa, and most preferably the feed stream pressure is from about 1.30 MPa to about 1.50 MPa, for example about 1.40 MPa. Preferably, the effluent stream pressure is from about 0.80 MPa to about 1.40 MPa, more preferably the effluent stream pressure is from about 0.85 MPa to about 1.20 MPa, and most preferably the effluent stream pressure is from about 0.90 MPa to about 1.10 MPa, for example about 1.00 MPa.

In accordance with the present invention, any of the temperature ranges mentioned above may be taken in combination with any of the pressure ranges described hereinbefore.

The term "heteropolyacid", as used herein and throughout the description of the present invention, is deemed to include inter alia; alkali, alkali earth, ammonium, free acids, bulky cation salts, and/or metal salts (where the salts may be either full or partial salts) of heteropolyacids. Hence, the heteropolyacids suitable for the present invention may be complex, high molecular weight anions comprising oxygen-linked polyvalent metal atoms. Typically, each anion comprises about 12 to about 18, oxygen-linked polyvalent metal atoms. The polyvalent metal atoms, known as peripheral atoms, surround one or more central atoms in a symmetrical manner. The peripheral atoms may be one or more of molybdenum, tungsten, vanadium, niobium, tantalum, or any other polyvalent metal. The central atoms are preferably silicon or phosphorus, but may alternatively comprise any one of a large variety of atoms from Groups I-VIII in the Periodic Table of elements. These include copper, beryllium, zinc, cobalt, nickel, boron, aluminium, gallium, iron, cerium, arsenic, antimony, bismuth, chromium, rhodium, silicon, germanium, tin, titanium, zirconium, vanadium, sulphur, tellurium, manganese nickel, platinum, thorium, hafnium, cerium, arsenic, vanadium, antimony ions, tellurium and iodine. Suitable heteropolyacids include Keggin, Wells-Dawson and Anderson-Evans-Perloff heteropolyacids. Specific examples of suitable heteropolyacids are as follows:

| 18-tungstophosphoric acid | $H_6[P_2W_{18}O_{62}].xH_2O$ |
|---|---|
| 12-tungstophosphoric acid | $H_3[PW_{12}O_{40}].xH_2O$ |
| 12-tungstosilicic acid | $H_4[SiW_{12}O_{40}].xH_2O$ |
| Cesium hydrogen tungstosilicate | $Cs_3H[SiW_{12}O_{40}].xH_2O$ | and the free acid or partial salts of the following heteropolyacids acids:

| Monopotassium tungstophosphate | $KH_5[P_2W_{18}O_{62}].xH_2O$ |
|---|---|
| Monosodium 12-tungstosilicic acid | $NaK_3[SiW_{12}O_{40}].xH_2O$ |
| Potassium tungstophosphate | $K_6[P_2W_{18}O_{62}].xH_2O$ |
| Ammonium molybdodiphosphate | $(NH_4)_6[P_2Mo_{18}O_{62}].xH_2O$ |
| Potassium molybdodivanado phosphate | $K_5[PMoV_2O_{40}].xH_2O$ |

In addition, mixtures of different heteropolyacids and salts can be employed. The preferred heteropolyacids for use in the process described by the present invention is any one or more heteropolyacid that is based on the Keggin or Wells-Dawson structures; more preferably the chosen heteropolyacid for use in the process described by the present invention is any one or more of the following: heteropolytungstic acid (such as silicotungstic acid and phosphotungstic acid), silicomolybdic acid and phosphomolybdic acid. Most preferably, the chosen heteropolyacid for use in the process described by the present invention is any one or more silicotungstic acid, for example 12-tungstosilicic acid ($H_4[SiW_{12}O_{40}].xH_2O$).

Preferably, the heteropolyacids employed according to the present invention may have molecular weights of more than about 700 and less than about 8500, preferably more than about 2800 and less than about 6000. Such heteropolyacids also include dimeric complexes.

The supported catalyst may be conveniently prepared by dissolving the chosen heteropolyacid in a suitable solvent, where suitable solvents include polar solvents such as water, ethers, alcohols, carboxylic acids, ketones and aldehydes; distilled water and/or ethanol being the most preferable solvents. The resulting acidic solution has a heteropolyacid concentration that is preferably comprised between about 10 to about 80 wt %, more preferably about 20 to about 70 wt % and most preferably about 30 to about 60 wt %. This said solution is then added to the chosen support (or alternatively the support is immersed in the solution). The actual volume of acidic solution added to the support is not restricted, and hence may be enough to achieve incipient wetness or wet impregnation, where wet impregnation (i.e. preparation using an excess acidic solution volume relative to pore volume of support), is the preferred method for the purposes of the present invention.

The resulting supported heteropolyacid may be modified, and various salts of heteropolyacid may then be formed in the aqueous solution either prior to, or during, impregnation of the acidic solution onto the support, by subjecting the supported heteropolyacid to a prolonged contact with a solution of a suitable metallic salt or by addition of phosphoric acid and/or other mineral acids.

When using a soluble metallic salt to modify the support, the salt is taken in the desired concentration, with the heteropolyacid solution. The support is then left to soak in the said acidic solution for a suitable duration (e.g. a few hours), optionally with periodic agitation or circulation, after which time it is filtered, using suitable means, in order to remove any excess acid.

When the salt is insoluble it is preferred to impregnate the catalyst with the HPA and then titrate with the salt precursor. This method can improve the dispersion of the HPA salt. Other techniques such as vacuum impregnation may also be employed.

The impregnated support may then be washed and dried. This may be achieved using any conventional separation technique, including, for example, decantation and/or filtration. Once recovered, the impregnated support may be dried, preferably by placing the support in an oven at elevated temperature. Alternatively, or additionally, a desiccator may be employed. On a commercial scale this drying stage is often achieved by a purge of hot inert gas such as nitrogen, where a flammable solvent has been used for impregnation, or air, where an aqueous solvent has been used for impregnation.

The amount of heteropolyacid impregnated on the resulting support is suitably in the range of about 10 wt % to about 80 wt % and preferably about 20 wt % to about 50 wt % based on the total weight of the heteropolyacid and the support. The weight of the catalyst on drying and the weight of the support used, may be used to obtain the weight of the acid on the support by deducting the latter from the former, giving the catalyst loading as 'g heteropolyacid/kg catalyst'. The catalyst loading in 'g heteropolyacid/liter support' can also be calculated by using the known or measured bulk density of the support. The preferred catalytic loading of heteropolyacid is about 150 to about 600 g heteropolyacid/kg Catalyst.

According to a preferred embodiment of the present invention the average heteropolyacid loading per surface area of the dried supported heteropolyacid catalyst is more than about 0.1 micro moles/m$^2$.

It should be noted that the polyvalent oxidation states and hydration states of the heteropolyacids stated previously and as represented in the typical formulae of some specific compounds only apply to the fresh acid before it is impregnated onto the support, and especially before it is subjected to the dehydration process conditions. The degree of hydration of the heteropolyacid may affect the acidity of the supported catalyst and hence its activity and selectivity. Thus, either or both of these actions of impregnation and dehydration process may change the hydration and oxidation state of the metals in the heteropolyacids, i.e. the actual catalytic species used, under the process conditions given, may not yield the hydration/oxidation states of the metals in the heteropolyacids used to impregnate the support. Naturally therefore it is to be expected that such hydration and oxidation states may also be different in the spent catalysts after reaction.

According to a preferred embodiment of the present invention, the amount of chloride present in/on the said heteropolyacid supported catalyst is less than about 40 ppm, preferably less than about 25 ppm and most preferably less than about 20 ppm.

The supported heteropolyacid catalyst used in the process of the present invention may be a fresh catalyst or a previously used catalyst. Thus, in one embodiment, at least a portion of the supported heteropolyacid catalyst has previously been employed in a process for the preparation of an ethene from a feed comprising ethanol (and optionally water and ethoxyethane). For example, at least a portion of the supported catalyst heteropolyacid may derive from an extract of heteropolyacid from a previously used catalyst i.e. from a partially deactivated material.

According to a further preferred embodiment of the present invention, the heteropolyacid supported catalyst is a heteropolytungstic acid supported catalyst having the following characteristic:

PV>0.6−0.3×[HPA loading/Surface Area of Catalyst]

wherein PV is the pore volume of the dried supported heteropolytungstic acid catalyst (measured in ml/g catalyst); HPA loading is the amount of heteropolyacid present in the dried supported heteropolyacid catalyst (measured in micro moles per gram of catalyst) and Surface Area of Catalyst is the surface area of the dried supported heteropolytungstic acid catalyst (measured in $m^2$ per gram of catalyst).

Suitable catalyst supports may be in a powder form or alternatively may be in a granular form, or in a pelletised form, a spherical form or as extrudates (including shaped particles) and include, but are not limited to, clays, bentonite, diatomous earth, titania, activated carbon, aluminosilicates e.g. montmorillonite, alumina, silica-alumina, silica-titania cogels, silica-zirconia cogels, carbon coated alumina, zeolites, zinc oxide, flame pyrolysed oxides. Supports can be mixed oxides, neutral or weakly basic oxides. Silica supports are preferred, such as silica gel supports and supports produced by the flame hydrolysis of $SiCl_4$. Preferred supports are substantially free of extraneous metals or elements which might adversely affect the catalytic activity of the system. Thus, suitable silica supports are at least about 99% w/w pure. Impurities amount to less than about 1% w/w, preferably less than about 0.60% w/w and most preferably less than about 0.30% w/w. The pore volume of the support is preferably more than about 0.50 ml/g and preferably more than about 0.8 ml/g.

Suitable silica supports include, but are not limited to any of the following: Grace Davison Davicat® Grade 57, Grace Davison Davicat® 1252, Grace Davison Davicat® SI 1254, Fuji Silysia CariAct® Q15, Fuji Silysia CariAct® Q10, Degussa Aerolyst® 3045 and Degussa Aerolyst® 3043. The average diameter of the support particles is about 2 to about 10 mm, preferably about 3 to about 6 mm. However, these particles may be crushed and sieved to smaller sizes of, for example, about 0.5 mm to about 2 mm, if desired.

The average pore radius (prior to impregnation with the heteropolyacid) of the support is about 10 to about 500 Å, preferably about 30 to about 175 Å, more preferably about 50 to about 150 Å and most preferably about 60 to about 120 Å. The BET surface area is preferably between about 50 and about 600 $m^2$/g and is most preferably between about 150 and about 400 $m^2$/g.

The BET surface area, pore volume, pore size distribution and average pore radius were determined from the nitrogen adsorption isotherm determined at 77K using a Micromeritics TRISTAR 3000 static volumetric adsorption analyser. The procedure used was an application of British Standard methods BS4359: Part 1:1984 'Recommendations for gas adsorption (BET) methods' and BS7591: Part 2:1992, 'Porosity and pore size distribution of materials'—Method of evaluation by gas adsorption. The resulting data were reduced using the BET method (over the pressure range 0.05-0.20 P/Po) and the Barrett, Joyner & Halenda (BJH) method (for pore diameters of 20-1000 Å) to yield the surface area and pore size distribution respectively.

Suitable references for the above data reduction methods are Brunauer, S, Emmett, P H, & Teller, E, J. Amer. Chem. Soc. 60, 309, (1938) and Barrett, E P, Joyner, L G & Halenda P P, J. Am Chem. Soc., 1951 73 373-380.

Samples of the supports and catalysts were out gassed for 16 hours at 120° C. under a vacuum of 5×10-3 Torr prior to analysis.

The present invention also provides a use of a reactor having an internal pressure of at least about 0.80 MPa but less than about 1.80 MPa, in a vapour phase chemical dehydration of a feed comprising ethanol, (and preferably further comprising water and ethoxyethane) and having a feed temperature of at least about 250° C. in the presence of a supported heteropolyacid catalyst, for preventing or reducing deactivation of the supported heteropolyacid catalyst. Preferred temperatures of the feed in this aspect of the invention are the same as those described hereinbefore. Preferably, there is provided use of a pressure of about 0.90 MPa to about 1.60 MPa inside the reactor. More preferably, there is provided use of a pressure of about 0.95 MPa to about 1.30 MPa inside the reactor. Most preferably, there is provided a use at a pressure of about 1.00 MPa to about 1.20 MPa inside the reactor. Preferred feed and effluent stream pressures in this aspect of the invention are the same as those described hereinbefore.

The present invention also provides a method for preventing or reducing deactivation of a supported heteropolyacid catalyst when used in the preparation of ethene by vapour phase chemical dehydration of a feed comprising ethanol, (and preferably further comprising water and ethoxyethane) in a reactor, wherein the feed has a temperature of at least about 250° C., said method comprising maintaining or adjusting the pressure inside the reactor to be at least about 0.80 MPa but less than about 1.80 MPa. Preferred temperatures of the feed in this aspect of the invention are the same as those described hereinbefore. Preferably, the pressure is maintained at, or adjusted to, a pressure of from about 0.90 MPa to about 1.60 MPa inside the reactor. More preferably, the pressure is maintained at, or adjusted to, a pressure of from about 0.95 MPa to about 1.30 MPa inside the reactor. Most preferably, the pressure is maintained at, or adjusted to, a pressure of from about 1.00 MPa to about 1.20 MPa inside the reactor. Preferred feed and effluent stream pressures in this aspect of the invention are the same as those described hereinbefore.

The present invention also provides products made by any of the processes described herein, and particularly with respect to the appended claims.

The present invention will now be illustrated by way of the following examples and with reference to the following figures:

FIG. 1: Graphical representation of ethylene productivity against time of catalyst exposure to a feed stream at 260° C.; and FIG. 2: Graphical representation of temperature (and pressure) on ethylene productivity.

CATALYST PREPARATION

A silicotungstic acid (STA) catalyst was used for conducting the dehydration reactions according to the following examples.

A pure silica support with a surface area of 147 m²/g, pore volume of 0.84 ml/g and a mean pore diameter of 230 Å was used for preparation of the STA catalyst. The catalyst was prepared by adding silica (512 g) to a solution of silicotungstic acid (508 g) in water (1249 g). Once the silicotungstic acid solution had fully impregnated the pores of the support the excess solution was drained, under gravity, from the support and this was then dried and crushed to a particle size of 100 to 200 µm before being loaded into the reactor tube.

The STA loading on the catalyst support as STA.6H$_2$O, on a dry weight basis, was estimated to be 24.5% w/w, based on the weight gained by the silica during the catalyst preparation.

Vapour Phase Dehydration Reactions

A mass of STA catalyst (as indicated in Table 1 below) prepared in accordance with the above method was loaded into a reactor tube having an isothermal bed and pressurised to 0.501 MPa under inert gas (nitrogen and helium) flow. The catalyst was heated at 2° C./min to 240° C. under a combined nitrogen (0.01500 mol/hr) and helium flow (0.00107 mol/hr) and held at this temperature for 8 hours before being cooled to 150° C.

Ethanol (0.04084 mol/hr) was then added to the nitrogen/helium flow and the temperature was increased at 2° C./min to 225° C. Once at 225° C. the feed pressure was increased at a rate of 0.1 MPa/min such that the pressure inside the reactor was increased to the value given in Table 1. Once at the desired pressure, the diethyl ether and water reagents were added to the ethanol, helium and nitrogen flow. At this point the flows of the feed components were adjusted to give ethanol (0.02677 mol/hr), diethyl ether (0.00776 mol/hr), water (0.00297 mol/hr), helium (0.00106 mol/hr) and nitrogen (0.01479 mol/hr).

Once the catalyst performance had stabilised at 225° C., typically after around 100 hrs, the catalyst temperature, which is the same as the feed temperature in this particular reactor, was increased to 260° C. and the ethylene productivity monitored versus time by on-line GC analysis. The results of dehydration experiments at varying pressure are presented in Table 1 below, showing the reactor ethylene productivity decreasing with time on stream.

TABLE 1

| Example | Mass of catalyst (mg) | Time on Stream at 260° C. (hrs) | Temperature (° C.) | Total Pressure (MPa) | Ethylene Productivity (mol/kg catalyst/hr) |
| --- | --- | --- | --- | --- | --- |
| Example 1 | 13.6 | 1.68 | 260 | 1.430 | 867 |
| Example 1 | 13.6 | 48.93 | 260 | 1.430 | 743 |
| Example 1 | 13.6 | 82.65 | 260 | 1.430 | 708 |
| Example 1 | 13.6 | 109.64 | 260 | 1.430 | 678 |
| Example 1 | 13.6 | 184.07 | 260 | 1.430 | 553 |
| Example 2 | 13.6 | 3.47 | 260 | 1.430 | 684 |
| Example 2 | 13.6 | 43.87 | 260 | 1.430 | 643 |
| Example 2 | 13.6 | 84.25 | 260 | 1.430 | 607 |
| Example 2 | 13.6 | 111.17 | 260 | 1.430 | 596 |
| Comparative Example 1 | 13.7 | 1.99 | 260 | 2.858 | 497 |
| Comparative Example 1 | 13.7 | 49.69 | 260 | 2.858 | 339 |
| Comparative Example 1 | 13.7 | 83.41 | 260 | 2.858 | 210 |
| Comparative Example 1 | 13.7 | 110.3 | 260 | 2.858 | 114 |
| Comparative Example 1 | 13.7 | 184.79 | 260 | 2.858 | 4 |
| Comparative Example 2 | 13.7 | 1.57 | 260 | 2.858 | 501 |
| Comparative Example 2 | 13.7 | 48.87 | 260 | 2.858 | 280 |
| Comparative Example 2 | 13.7 | 82.67 | 260 | 2.858 | 183 |
| Comparative Example 2 | 13.7 | 109.67 | 260 | 2.858 | 63 |
| Comparative Example 2 | 13.7 | 183.83 | 260 | 2.858 | 7 |
| Comparative Example 3 | 13.5 | 6.62 | 260 | 2.858 | 494 |
| Comparative Example 3 | 13.5 | 46.95 | 260 | 2.858 | 342 |
| Comparative Example 3 | 13.5 | 80.65 | 260 | 2.858 | 170 |
| Comparative Example 3 | 13.5 | 114.26 | 260 | 2.858 | 83 |
| Comparative Example 3 | 13.5 | 181.49 | 260 | 2.858 | 5 |
| Comparative Example 4 | 13.6 | 2.82 | 260 | 2.858 | 388 |
| Comparative Example 4 | 13.6 | 43.2 | 260 | 2.858 | 289 |
| Comparative Example 4 | 13.6 | 83.59 | 260 | 2.858 | 102 |
| Comparative Example 4 | 13.6 | 110.52 | 260 | 2.858 | 17 |

The results in Table 1, which are represented graphically in FIG. 1, illustrate the benefits of the process of the invention with regard to catalyst lifetime. It is clear from FIG. 1 that ethylene productivity remains high with Examples 1 and 2, which are conducted at a pressure according to the present invention in a high-temperature (260° C.) dehydration reaction, for a significantly longer period of time compared with Comparative Examples 1 to 4, which are conducted at pressures not in accordance with the present invention.

Notably, in a high-temperature dehydration (260° C.) process, ethylene productivity is substantially diminished with Comparative Examples 1 to 4 after only 100 hours reaction time at high temperature. This is indicative of substantial catalyst deactivation. Moreover, as is clear from FIG. 1, near complete catalyst deactivation is observed with Comparative Examples 1 to 4 after 180 hours reaction time at high temperature.

In addition, the results in Table 1 also demonstrate that Examples 1 and 2 have significantly higher maximum ethylene productivities (867 and 684 g/Kg catalyst/hr respectively) compared with Comparative Examples 1 to 4 (497, 501, 494 and 388 g/Kg catalyst/hr respectively). Thus, it is clear that the particular combination of temperature and pressure of the dehydration process according to the present invention both increases ethylene productivity and reduces catalyst deactivation.

In a further set of experiments, dehydration reactions were conducted with the same STA catalyst in the same manner as described above, apart from after the stabilisation period at 225° C., the reaction temperature was modified to 220, 240, 260, 280 or 295° C. and ethylene productivity was monitored versus time by on-line GC analysis. The results of these additional dehydration experiments are presented in Table 2 below, also showing a benefit to ethylene productivity when operating according to the present invention.

TABLE 2

| Example | Mass of catalyst (mg) | Time on Stream at temperature (hrs) | Temperature (° C.) | Total Pressure (MPa) | Ethylene Productivity (mol/kg catalyst/hr) |
|---|---|---|---|---|---|
| Example A | 13.7 | 2 | 225 | 2.858 | 42 |
| Example A | 13.6 | 3.94 | 240 | 2.858 | 109 |
| Example A | 13.7 | 1.99 | 260 | 2.858 | 497 |
| Example A | 13.7 | 5.09 | 280 | 2.858 | 1058 |
| Example A | 13.6 | 7.41 | 295 | 2.858 | 1326 |
| Example B | 13.69 | 1.69 | 225 | 2.858 | 39 |
| Example B | 13.69 | 1.57 | 260 | 2.858 | 501 |
| Example C | 13.6 | 1.36 | 220 | 1.430 | 100 |
| Example C | 13.6 | 1.37 | 225 | 1.430 | 152 |
| Example C | 13.6 | 1.68 | 225 | 1.430 | 140 |
| Example C | 13.6 | 4.73 | 225 | 1.430 | 125 |
| Example C | 13.6 | 6.2 | 225 | 1.430 | 119 |
| Example C | 13.6 | 4.72 | 240 | 1.430 | 313 |
| Example C | 13.6 | 1.68 | 260 | 1.430 | 867 |
| Example C | 13.6 | 6.19 | 280 | 1.430 | 1463 |
| Example D | 13.5 | 6.62 | 225 | 2.858 | 28 |
| Example D | 13.5 | 6.62 | 260 | 2.858 | 494 |
| Example E | 13.6 | 1.36 | 220 | 2.144 | 46 |
| Example E | 13.6 | 1.37 | 225 | 2.144 | 85 |
| Example E | 13.7 | 2.56 | 225 | 2.144 | 67 |
| Example E | 13.6 | 4.66 | 225 | 2.144 | 64 |
| Example E | 13.6 | 6.65 | 225 | 2.144 | 65 |
| Example E | 13.6 | 4.2 | 240 | 2.144 | 208 |
| Example E | 13.7 | 2.1 | 260 | 2.144 | 695 |
| Example E | 13.6 | 6.2 | 280 | 2.144 | 1460 |
| Example F | 13.6 | 6 | 220 | 1.430 | 94 |
| Example F | 13.6 | 2.63 | 225 | 1.430 | 147 |
| Example F | 13.6 | 3.47 | 260 | 1.430 | 684 |
| Example G | 13.6 | 2.82 | 260 | 2.858 | 388 |

Figure 2:
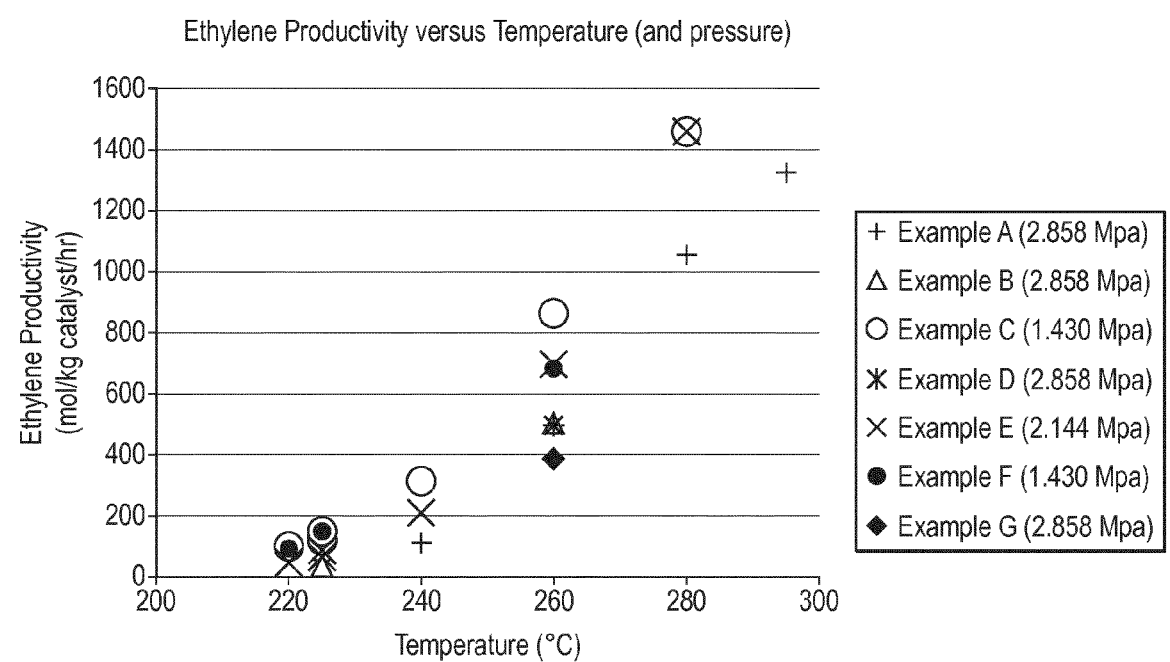

The results in Table 2, which are represented graphically in FIG. 2, illustrate the benefits of the process of the invention with regard to ethylene productivity. As is clear from FIG. 2, ethylene productivity is generally increased by increasing the temperature at which the dehydration process is conducted, for all pressures tested. However, what is also clear from FIG. 2 is that conducting the dehydration reaction at a pressure in accordance with the present invention (e.g. as in the case for Examples C and F) leads to superior ethylene productivities compared with reactions conducted at high pressure (e.g. Examples A and G).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope and spirit of this invention.

The invention claimed is:

1. A process for preparation of ethene by vapour phase chemical dehydration of a feed comprising ethanol, said process comprising contacting a supported heteropolyacid catalyst in a reactor with the feed, wherein the feed has a temperature of at least 250° C. and pressure inside the reactor is at least 0.80 MPa but less than 1.80 MPa.

2. The process according to claim 1, wherein the process is conducted at a feed temperature between 252° C. and 325° C.

3. The process according to claim 1, wherein the pressure inside the reactor is from 0.90 MPa to 1.60 MPa.

4. The process according to claim 1, comprising a feed stream pressure from 1.00 MPa to 1.80 MPa.

5. The process according to claim 1, comprising an effluent stream pressure from 0.80 MPa to 1.40 MPa.

6. The process according to claim 1, wherein the feed further comprises water and/or ethoxyethane.

7. The process according to claim 1, wherein the catalyst is provided in a form of one or more catalyst beds in the reactor.

8. The process according to claim 7 wherein the catalyst is provided in the form of multiple catalyst beds, wherein the multiple catalyst beds are arranged in series or in parallel.

9. The process according to claim 7, wherein at least one of the one or more catalyst beds is a tubular fixed bed or a fluid bed.

10. The process according to claim 1, wherein the heteropolyacid in the supported heteropolyacid catalyst is in an amount in the range of from 10 wt. % to 50 wt. % based on total weight of the supported heteropolyacid catalyst.

11. The process according to claim 1, wherein at least a portion of the supported heteropolyacid catalyst has previously been employed in a process for the preparation of an ethene from a feed comprising ethanol.

12. The process according to claim 1, wherein the supported heteropolyacid catalyst is a supported heteropolytungstic acid catalyst.

13. The process according to claim 12, wherein the supported heteropolytungstic catalyst is a supported silicotungstic acid catalyst.

14. The process according to claim 12 characterised in that the supported heteropolytungstic acid catalyst has a characteristic of:

PV>0.6−0.3×[HPA loading/Surface Area of Catalyst]

wherein PV is the pore volume of dried supported heteropolytungstic acid catalyst (measured in ml/g catalyst); HPA loading is an amount of heteropolyacid present in the dried supported heteropolyacid catalyst (measured in micro moles per gram of catalyst) and Surface Area of Catalyst is surface area of the dried supported heteropolytungstic acid catalyst (measured in $m^2$ per gram of catalyst).

15. The process according to claim 13, wherein the supported heteropolytungstic catalyst is 12-tungstosilicic acid ($H_4[SiW_{12}O_{40}].xH_2O$).

16. The process according to claim 1, wherein the process is conducted at a feed temperature between at least 255° C. to 325° C.

17. The process according to claim 3, wherein the pressure inside the reactor is selected from:
from 0.95 MPa to 1.30 MPa; or
from 1.00 MPa to 1.20 MPa.

18. The process according to claim 4, comprising a feed stream pressure selected from:

from 1.20 MPa 1.60 MPa; or
from 1.30 MPa to 1.50 MPa.

19. The process according to claim 1, comprising an effluent stream pressure selected from:
from 0.85 MPa to 1.20 MPa; or
from 0.90 MPa to 1.10 MPa.

20. A process for preparation of ethene by vapour phase chemical dehydration of a feed comprising ethanol, said process comprising contacting a supported heteropolyacid catalyst in a reactor with the feed, wherein the feed has a temperature of at least 250° C. and pressure inside the reactor is at least 0.80 MPa but less than 1.80 MPa,
   wherein at least a portion of the supported heteropolyacid catalyst has previously been employed in preparing an ethene from a feed comprising ethanol, water and ethoxyethane.

\* \* \* \* \*